(12) United States Patent
Subramani et al.

(10) Patent No.: US 10,584,085 B2
(45) Date of Patent: Mar. 10, 2020

(54) PROCESS FOR ETHERIFICATION OF MIXED OLEFINIC LIGHT NAPHTHA AND SIMULTANEOUS REDUCTION OF METHANOL IN THE PRODUCT

(71) Applicant: INDIAN OIL CORPORATION LIMITED, Mumbai (IN)

(72) Inventors: Saravanan Subramani, Faridabad (IN); Prosenjit Maji, Faridabad (IN); Reshmi Manna, Faridabad (IN); Pushkar Varshney, Faridabad (IN); Latoor Lal Saroya, Faridabad (IN); Kamlesh Gupta, Faridabad (IN); Dheer Singh, Faridabad (IN); Debasis Bhattacharyya, Faridabad (IN); Sanjiv Kumar Mazumdar, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 0 days.

(21) Appl. No.: 16/237,319

(22) Filed: Dec. 31, 2018

(65) Prior Publication Data

US 2019/0248720 A1 Aug. 15, 2019

(30) Foreign Application Priority Data

Feb. 14, 2018 (IN) .............................. 201821005594

(51) Int. Cl.
| | | |
|---|---|---|
| *C07C 41/06* | (2006.01) | |
| *C07C 41/09* | (2006.01) | |
| *C10L 1/02* | (2006.01) | |

(52) U.S. Cl.
CPC .............. *C07C 41/06* (2013.01); *C07C 41/09* (2013.01); *C10L 1/023* (2013.01)

(58) Field of Classification Search
CPC .......... C07C 41/06; C07C 41/09; C10L 1/023
See application file for complete search history.

(56) References Cited

U.S. PATENT DOCUMENTS

| | | | | |
|---|---|---|---|---|
| 2,480,940 | A * | 9/1949 | Kreps | ..................... C07C 41/06 568/697 |
| 4,361,422 | A | 11/1982 | Derrien et al. | |
| 4,546,206 | A * | 10/1985 | Neier | ..................... C07C 41/06 568/697 |
| 4,826,507 | A | 5/1989 | Harandi et al. | |
| 5,166,455 | A | 11/1992 | Chin et al. | |
| 2006/0065574 | A1 * | 3/2006 | Koskinen | ............... C10G 50/00 208/49 |

FOREIGN PATENT DOCUMENTS

| | | |
|---|---|---|
| EP | 0498975 A1 | 8/1992 |
| EP | 0718269 A1 | 6/1996 |

OTHER PUBLICATIONS

Morales et al. ("Thermodynamic study for the production of methyl tert-amyl ether. Prediction of chemical equilibrium", Revista del Instituto Mexicano del Petroleo, Vo. 19, Issue 4, 1987, pp. 76-79).*
Girolamo, M.D., and Sanfilipppo, D., Encyclopaedia of Hydrocarbons: Refining and Petrochemicals, vol. 2, (Mar. 2006), index only.
Linnekoski, A., J., et. al., "Simultaneous Isomerization and Etherification of Isoamylenes, " Industrial Engineering Chemistry Research vol. 38, Issue 12 pp. 4563-4570 (Nov. 1999).
Soto, R., et al., "Equilibrium conversion, selectivity and yield optimization of the simultaneous liquid-phase etherification of isobutene and isoamylenes with ethanol over Amberlyst™ 35," Fuel Processing Technology, vol. 142, pp. 201-211 (Feb. 2016).
Soto, R., et al., "Equilibrium of the simultaneous etherification of isobutene and isoamylenes with ethanol in liquid-phase," Chemical Engineering Research and Design, vol. 92, Issue 4, pp. 644-656 (Jul. 2013).

* cited by examiner

*Primary Examiner* — Rosalynd A Keys
(74) *Attorney, Agent, or Firm* — Maschoff Brennan

(57) ABSTRACT

The present invention relates to a process for etherification of mixed olefinic light naphtha boiling in the range of C5-90° C. cut with simultaneous minimization of unreacted methanol concentration in the product. The etherification of mixed olefinic light naphtha produces the high octane blending component which can be blended directly in the gasoline pool without any recovery of the feed oxygenates like methanol, ethanol etc. which conventionally uses energy intensive separation processes.

7 Claims, 2 Drawing Sheets

PROCESS FOR ETHERIFICATION OF MIXED OLEFINIC LIGHT NAPHTHA AND SIMULTANEOUS REDUCTION OF METHANOL IN THE PRODUCT

FIELD OF THE INVENTION

This invention relates to a process for etherification of mixed olefinic light naphtha boiling in the range of C5-90° C. cut with simultaneous minimization of un-reacted methanol concentration in the product. The etherification of mixed olefinic light naphtha produces the high octane blending component which can be blended directly in the gasoline pool without any recovery of the feed oxygenates like methanol, ethanol etc. which conventionally uses energy intensive separation processes.

BACKGROUND OF THE INVENTION

In the petroleum refining and petrochemical industry lot of olefinic naphtha streams are generated through various thermal and catalytic cracking processes such as delayed coking, steam cracking, fluid catalytic cracking (FCC), visbreaking etc. These processes generates olefinic naphtha streams comprising wide range of olefinic components from C5 to C14 and higher. Conventional TAME process involves various steps that include separation of the C5 fraction from FCC naphtha, de-sulfurize the C5 fraction, selective di-olefin saturation, TAME reaction and methanol separation cum recycling. Methanol is always used in excess to achieve the equilibrium conversion. Some of the prior art describes the method to route the excess methanol in the second reactor for conversion into lighter olefins or gasoline.

Etherification of isoamylenes mainly 2-methyl-1-butene and 2-methyl-2-butene is a well-known process which utilizes acidic catalytic system for production of Tertiary amyl methyl ether (TAME). This reaction is exothermic. In order to suppress the side reaction and also to improve the yield of TAME, methanol is always kept in excess over the stoichiometric ratio required for TAME production.

EP0498975A1 discloses a process for conversion on isoamylene into TAME by reacting with methanol in presence of modified acidic smectite clay catalysts.

EP0718269A1 describes a process for production of tertiary alkyl ethers by feeding $C_5$ hydrocarbon stream to an etherification reactor and recycling the remaining stream in the same reactor after converting the linear pentenes into reactive isoamylenes.

U.S. Pat. No. 4,361,422 discloses a process for hydrogenation and etherification of unsaturated C5 streams to increase the octane number and to decrease the mono-olefin content.

U.S. Pat. No. 4,826,507 discloses a process for conversion of $C_4$+ isoalkenes into ethers rich in MTBE and TAME by using excess methanol in the feed. The excess methanol was not recycled as per the conventional methods, however it is passed for concurrent conversion with the portion of effluent stream to conversion reactor wherein the presence of zeolite catalyst system, the alcohols and the olefins present in the stream are converted to gasoline. The second portion of the reactor section is generally called as methanol to gasoline process (MTG).

U.S. Pat. No. 5,166,455 discloses a process for conversion of $C_5$-$C_7$ olefinic hydrocarbons such as those contained in FCC light naphtha to isobutene and isoamylene rich streams for production for MTBE and TAME. The process involves the initial separation of $C_5$ fraction of the feed stream which is converted to TAME. The $C_6$-$C_7$ fraction plus un-reacted $C_5$'s are converted into isobutylene and isoamylene rich stream by cracking with medium pore zeolite catalyst which is then used as feed stream for etherification to MTBE and TAME.

SUMMARY OF THE INVENTION

In the present invention, mixed olefinic light naphtha boiling in the range of C5-90° C. directly routed to etherification reaction zone wherein the mixed olefins including C5, C6 iso-olefins reacts with the methanol and produces mixed ethers in the presence of ion-exchange resin catalysts. More preferably in the present invention, mixed olefinic light naphtha boiling in the range of C5-70° C. directly routed to etherification reaction zone wherein the mixed olefins including C5, C6 iso-olefins reacts with the methanol and produces mixed ethers in the presence of ion-exchange resin catalysts.

Present invention also discloses a novel route for reducing the methanol content in the product without the energy intensive conventional distillation/separation columns which comprises an additional second reaction zone where in dehydration of tertiary butyl alcohol (TBA) to isobutene and subsequent etherification with methanol takes place. Second reaction zone is connected in series with the etherification reaction zone. Entire product of etherification reaction zone is routed to second reaction zone where in tertiary butyl alcohol is added precisely to reduce the methanol content in the product from etherification reaction zone. This two reaction zone concept is cost effective and simple when compared to the much complicated conventional separation process used for recovery of excess methanol.

Advantages of the Invention

The advantages of the present invention over the prior art are listed as follows:

Methanol recovery using multiple fractionation columns are resolved by optimizing the process conditions for ether production with least possible methanol in the product and subsequent treatment of the product with TBA in the second reaction zone for minimizing the methanol concentration in the final product.

Also direct routing of feed to the reaction zones minimizes the feed pre-fractionation and treatment cost.

Another advantage of the present invention is formation of mixed ethers including C5, C6, C7 and C8+ ethers which enhance the octane of the stream while reducing its olefin concentration.

DETAILED DESCRIPTION OF THE INVENTION

Figure 1:
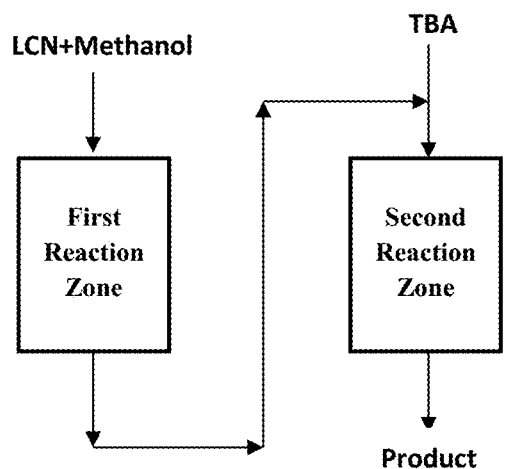
FIG. 1 illustrates scheme 1 related to two reaction zone system.

Accordingly, present invention provides a process for production of mixed ethers from mixed olefinic naphtha stream using ion exchange resin catalyst in a multiple reaction zone system.

Present invention further provides the process for production of mixed ethers like $C_5$, $C_6$, $C_7$ and $C_8+$ ethers which increases the blending octane number of the final product.

In detail, the present invention utilizes two different reaction zones, viz. etherification and dehydration cum etherification which offer the flexibility for maintaining the reaction environment conducive for etherification and dehydration application favoring the selective production of respective ethers. Also it provides a flexibility to operate the two different reaction zones at different operating conditions.

Also, the advantage of the present invention is that the elimination of pre-fractionation section, selective hydrogenation section and methanol recovery section which significantly reduces the capital and operating cost.

It is further feature of present invention that the product from the process is directly blended without any further hydrogenation and treatment.

Another feature of present invention is that there is no requirement of recycling of methanol as it is reduced below the level of 0.5 wt % in the product in the etherification zone and less than 1000 PPM in the second reaction zone.

It is yet another feature of present invention that the significant reduction of mono-olefins due to reaction of mixed olefins with the methanol at the optimized reaction conditions.

Accordingly, present invention provides a process for production of mixed ethers product from mixed olefinic naphtha stream boiling in the range of C5-90° C. cut comprising isoamylene, the process comprising etherifying the mixed olefinic naphtha stream with methanol in an etherification reaction zone, wherein:
the reaction is carried out at a pressure above 16 bar and the stoichiometric mole ratio of methanol to isoamylene is in the range of 0.5-0.9, to obtain mixed ethers product comprising tertiary amyl methyl ether.

In the present invention, the mixed olefinic naphtha stream boiling in the range of C5-90° C. cut comprises C5, C6, and C7 iso-olefins and selected from isoamylene, isohexenes, and iso-heptenes.

In the present invention, the process is conducted in presence of an ion-exchange resin catalyst.

In the present invention, the pressure is in the range of 16-20 bar.

In the present invention, the process is conducted at a temperature in the range of 70 to 90° C.

In the present invention, the methanol in the mixed ethers product is in the range of 0.2-0.5 wt. %.

In the present invention, the mixed ethers product comprises tertiary amyl methyl ether in the range of 10 to 20 wt. %.

In the present invention, the process is carried out in multiple etherification reaction zones, operating in series or parallel configuration.

Accordingly, present invention also provides a process for production of mixed ethers from mixed olefinic naphtha stream boiling in the range of C5-90° C. cut comprising isoamylene, the process comprising:
(i) reacting the mixed olefinic naphtha stream with methanol in a first etherification reaction zone, wherein the reaction is carried out at a pressure above 16 bar and the stoichiometric mole ratio of methanol to isoamylene is in the range of 0.5-0.9 to obtain a first product comprising tertiary amyl methyl ether; and
(ii) reacting the product of step (i) and tertiary butyl alcohol in a second etherification reaction zone to obtain a second product comprising methyl tertiary butyl ether,
wherein the first product is cooled prior to reaction in step (ii).

In the present invention, the tertiary butyl alcohol is produced in the second etherification reaction zone by reacting mixed olefinic C4 stream with water.

In the present invention, the reaction in the first etherification reaction zone is carried out at a pressure in the range of 16-20 bar and at a temperature in the range of 70-90° C.

In the present invention, the reaction in the second etherification reaction zone is carried out at a pressure of about 6-8 bar and at a temperature in the range of 60-70° C.

In the present invention, the mole ratio of tertiary butyl alcohol to methanol is maintained in the range of 0.5-1 in the second etherification reaction zone.

In the present invention, the methanol in the product of first etherification reaction zone is in the range of 0.25-0.5 wt. % and in product of the second etherification reaction zone is in the range of 0.03-0.05 wt. % and tertiary amyl methyl ether in the range of 16 to 18 wt. %.

Accordingly, present invention also provides a process for production of mixed ethers from mixed olefinic naphtha stream boiling in the range of C5-90° C. cut comprising isoamylene, the process comprising:
(i) reacting the mixed olefinic naphtha stream with methanol in a first etherification reaction zone, wherein the reaction is carried out at a pressure above 16 bar and the ratio of methanol to isoamylene is in the range of 0.5-0.9 to obtain a first ether product, which comprises TAME;
(ii) feeding the first ether product of step (i) in a product separation column to separate heavier ether product from unconverted mixed olefinic naphtha stream and methanol; and
(iii) feeding the unconverted product from the product separation column to a second etherification reactor, operating at the same conditions as that of first etherification reaction zone.

In the present invention, the mixed olefinic naphtha stream reacts with methanol in a first etherification reaction zone at a temperature in the range of 70 to 90° C.

In the present invention, the mixed ethers product comprises tertiary amyl methyl ether in the range of 19 to 20 wt. % and methanol in the range of 0.03-0.05 wt. %.

In the present invention, the space velocity with respect to isoamylene is maintained in the range of 1-2 $hr^{-1}$.

In one feature of the present invention as depicted in scheme 1 (FIG. 1), the entire product from first reaction zone is routed to second reaction zone wherein the unreacted methanol present in the product of the first reaction zone or etherification zone is treated with TBA in the second reaction zone for minimization of methanol in the final product. The objective of the second reaction zone is to reduce the methanol concentration in the final product by dehydrating the TBA which in turn produces isobutylene and water. The isobutylene readily reacts with the methanol present in the product to produce MTBE, which in turn reduces the methanol concentration in the product as well as increases the ether concentration in the product. This integrated single step process enhances the octane number of the stream by 4-6 units when compared to the octane number of the feed stream.

Figure 2:
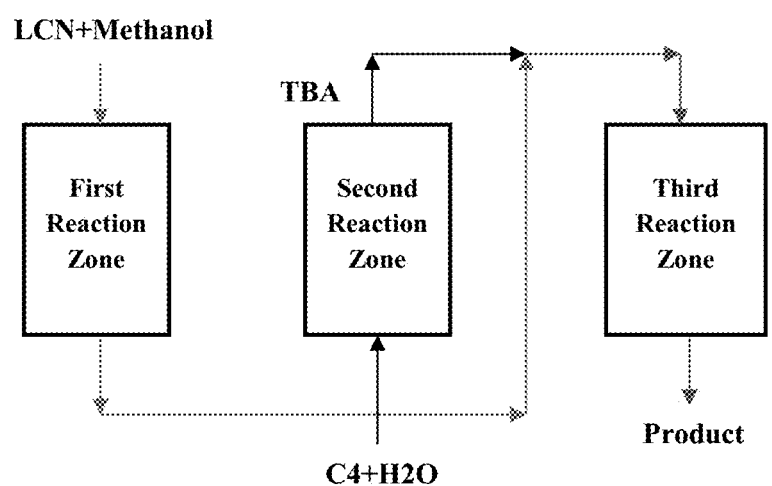
FIG. 2 illustrates scheme 2 related to three reaction zone system wherein TBA is produced in the second reaction zone by reacting mixed olefinic C4 stream with water.

In another feature of the present invention as depicted in scheme 2 (FIG. 2), the TBA is produced in the second reaction zone by reacting mixed olefinic C4 stream with water. TBA and other alcohols produced in the second reaction zone is routed to third reaction zone where it reacts with the first reaction zone product in which the excess methanol reacts with isobutylene obtained through dehydration of TBA to produce mixed ether in the third reaction zone. Alternatively pure TBA can be obtained from second reaction zone and routed to high pressure separation zone in order to remove the unreacted C4 components and also to draw an extra stream as valuable byproduct.

Figure 3:
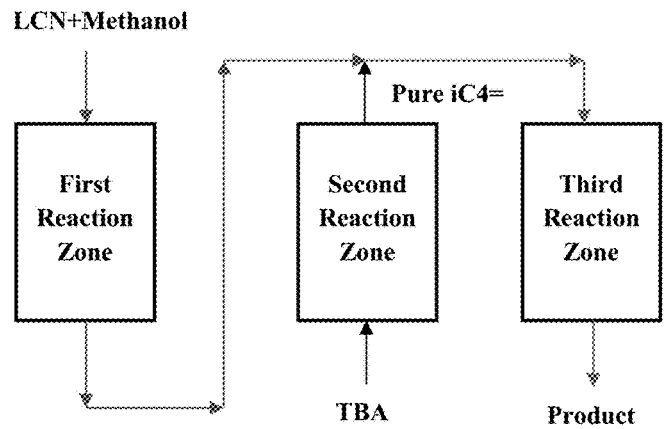
FIG. 3 illustrates scheme 3 related to three reaction zone system wherein TBA is passed through the second reaction zone.

In another feature of the present invention as depicted in scheme 3 (FIG. 3), the TBA is passed through the second reaction zone where it is dehydrated to pure isobutylene. This isobutylene is routed to third reaction zone in a precisely controlled quantity to meet the stoichiometric requirement of excess methanol present in the first reaction zone product.

Figure 4:
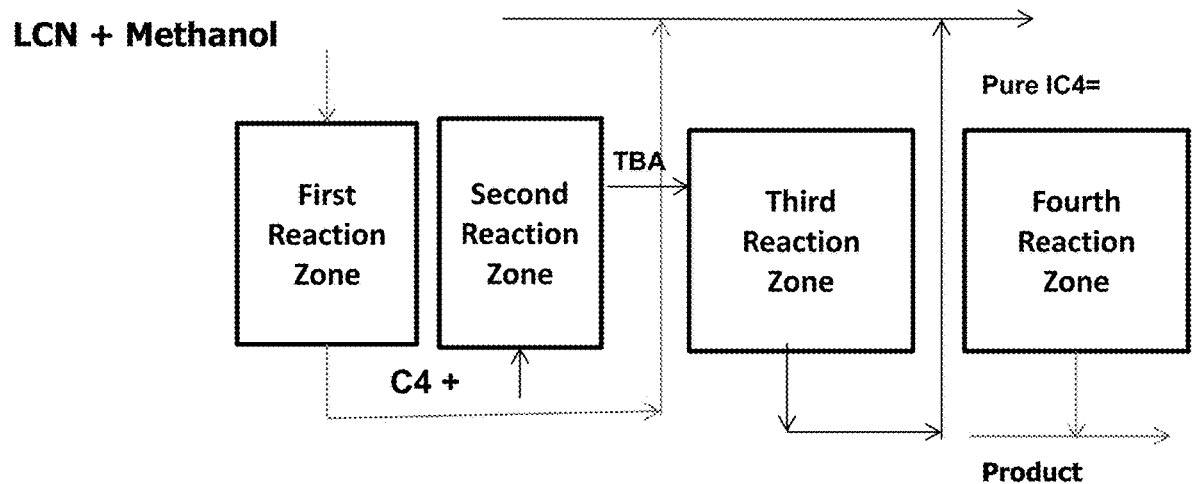
FIG. 4: illustrates scheme 4 related to four reaction zone system.

In another feature of the present invention as depicted in scheme 4 (FIG. 4), the TBA which is produced in the second reaction zone is routed to third reaction zone where dehydration takes place to produce pure isobutylene. This isobutylene is routed to fourth reaction zone in a precisely controlled quantity to meet the stoichiometric requirement of excess methanol present in the first reaction zone product.

Yet in another feature, the present invention provides the method to reduce the methanol content in product without significant loss in the product yield. It is achieved by providing the two reaction zone system. In the first reaction zone, mixed olefinic light naphtha stream is reacted with methanol wherein the majority of iso-olefins particularly iso-amylenes and C6 iso-olefins are converted to mixed ethers like TAME and C7 ethers. The process conditions are optimized in such a way that, the ethers yield is maximized with the minimum possible presence of methanol in the product.

In the detailed description of the present invention, mixed olefinic light naphtha boiling in the range of C5-90° C. directly routed to etherification reaction zone wherein the mixed olefins including C5, C6 iso-olefins present in the light cracked naphtha (LCN) fraction reacts with the methanol and produces mixed ethers including C5, C6, C7 and C8+ ethers in the presence of cationic ion-exchange resin as a catalysts. More preferably mixed olefinic light naphtha boiling in the range of C5-70° C. directly routed to etherification reaction zone wherein the mixed olefins including C5, C6 iso-olefins present in the light cracked naphtha (LCN) fraction reacts with the methanol and produces mixed ethers including C5, C6 and C7+ ethers in the presence of cationic ion-exchange resin as a catalysts. C6, C7 and C7+ ethers are produced in etherification reaction zone (First reaction zone) whereas C5 ether is produced in second reaction zone. C6 ether is produced from reaction between the iso-amylenes and methanol and C7 ethers are produced from reaction between iso-hexenes and methanol. C7+ ethers are heavier ethers formed during the process of mixed etherification. All the products like C5, C6 and C7 ethers formed during the process are part of the product stream along with unconverted hydrocarbon streams and there is no separation of the same is required as it can be directly blended in the gasoline pool without any further treatment.

The following non-limiting examples illustrate in details about the invention. However, they are, not intended to be limiting the scope of present invention in any way.

EXAMPLE-1

Effect of Pressure

TABLE 1

| Run No. | Methanol/ isoamylenes in feed, mol/mol | Temperature, ° C. | Pressure, bar | Total Olefins reduction, wt % | Ether Yield on total feed basis, wt % | Unreacted methanol concentration in product, Wt % |
| --- | --- | --- | --- | --- | --- | --- |
| 1 | 0.7 | 81.0 | 2.0 | 18.76 | 3.60 | 4.10 |
| 2 | 0.5 | 84.5 | 8.0 | 21.74 | 5.89 | 3.39 |
| 3 | 0.5 | 85.0 | 16.0 | 20.95 | 13.39 | 0.29 |
| 4 | 0.5 | 86.0 | 20.0 | 20.59 | 9.82 | 0.21 |

This example (table 1) shows the effect of pressure on ether yield and reduction in olefin content. With the increase in pressure from 2 bar to 20 bar, it is observed that the yield of ether is increased from 3.60 to 13.39 wt %. However above 16 bar, there is no significant change in the ether yield. Although, it is conventionally believed that for the liquid phase reaction pressure is not a critical parameter, it is surprisingly seen that the pressure has an impact on both ether yield and unreacted methanol concentration in product because conventional process utilizes pressure in the range of 3-8 bar. In conventional processes pure Iso-amylenes or specific C5 streams are used for production of pure TAME product. It utilizes higher methanol to iso-amylene ratio which is normally in the range of 1.25-1.3 and also utilizes reactive distillation column, which is energy intensive to favour the thermodynamic equilibrium. However both the reactive distillation and the excess methanol recovery are energy intensive which is overcome by the present invention.

EXAMPLE-2

Effect of Temperature

TABLE 2

| Run No. | Methanol/ isoamylenes in feed, mol/mol | Temperature (° C.) | Pressure (bar) | Total Olefins reduction, wt % | Ether Yield on total feed basis, wt % | Unreacted methanol concentration in product, Wt % |
|---|---|---|---|---|---|---|
| 1 | 0.5 | 51.3 | 20.0 | 21.70 | 7.05 | 2.81 |
| 2 | 0.5 | 61.5 | 20.0 | 24.56 | 9.53 | 1.64 |
| 3 | 0.5 | 70.6 | 20.0 | 22.36 | 9.73 | 1.2 |
| 4 | 0.5 | 86.0 | 20.0 | 20.59 | 9.82 | 0.21 |
| 5 | 0.5 | 100.8 | 20.0 | 17.44 | 8.14 | 3.00 |

This example (table-2) shows the effect of temperature on ether yield and reduction in olefin content. It is observed that below 60° C., ether yield is low and beyond 86° C., ether yield decreases gradually. Hence optimum temperature is a critical parameter on both ether yield and unreacted methanol concentration in product.

The effect of temperature is explained from the equilibrium aspects of the etherification reaction. There are three stoichiometrically independent reactions involved in the etherification of isoamylenes with methanol:

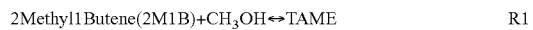

2Methyl1Butene(2M1B)+CH₃OH↔TAME    R1

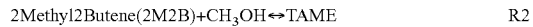

2Methyl2Butene(2M2B)+CH₃OH↔TAME    R2

2M1B↔2M2B    R3

Reactions, R1, R2 and R3 are combined to produce TAME. Addition of reaction R2 and R3 gives R1. Literature data (Ref. R. Soto et al./*Chemical Engineering Research and Design* 92 (2014) 644-656, R. Soto et al./*Fuel Processing Technology* 142 (2016) 201-211, Juha A. Linnekoski et al./*Ind. Eng. Chem. Res.* 38 (1999) 4563-4570, *Encyclopaedia of Hydrocarbons Volume II/Refining and Petrochemicals* 193-209) shows that the reaction, R1 decreases more rapidly with temperature than R2 as it is having the higher exothermicity and R3 almost has no effect of temperature. Reaction rate of R1 is higher than R2. Hence, as R1 and R2 both decreases with temperature, etherification decreases with temperature but R3 continues till higher temperature and R2 and R3 combine produce ethers at higher temperature. At the optimum temperature etherification maximize from both the isoamylenes, in this example which is 70-90° C.

EXAMPLE-3

TABLE 3

| Run No. | Methanol/ isoamylenes in feed, mol/mol | Temperature (deg C.) | Pressure (bar) | Ether Yield on total feed basis, wt % | Unreacted methanol concentration in product, wt % |
|---|---|---|---|---|---|
| 1 | 0.5 | 85.0 | 16.0 | 13.52 | 0.21 |
| 2 | 0.7 | 87.0 | 16.0 | 12.76 | 0.30 |
| 3 | 0.9 | 85.0 | 16.0 | 18.82 | 0.50 |
| 4 | 1.0 | 83.5 | 16.0 | 19.61 | 0.95 |
| 5 | 1.1 | 85.5 | 16.0 | 20.21 | 2.3 |
| 6 | 1.3 | 84.3 | 16.0 | 19.84 | 5.38 |

This example (table 3) shows the effect of methanol to isoamylenes ratio in feed of ether yield and unreacted methanol concentration in the product. It is observed that, with increasing the methanol to isoamylenes ratio in feed, ether yield increases proportionally but unreacted methanol concentration in the product also increases. Hence an optimum concentration of 0.5-0.9 methanol to isoamylenes ratio is maintained in the present invention to achieve the desired yield and also the lower concentration of methanol in product.

EXAMPLE-4

This example shows the formation of MTBE in the second reaction zone 75 wt % of pure TBA and 25 wt % of pure methanol is mixed and the same is subjected to reaction under the specific process conditions in presence of catalyst. The formation of MTBE is confirmed through the detailed hydrocarbon analyzer as well in HR GC-MS. About 50% of MTBE, 13% and 26% unconverted methanol and TBA are present in the product respectively. This confirms the formation of MTBE when pure TBA is mixed with pure methanol and subjected to reaction in second reaction zone.

EXAMPLE-5

This example shows the non ideal behavior of TBA and Methanol in presence of TAME One of the feed for this example is the product of first reaction zone or etherification zone. The first reaction zone product is operated at optimized process conditions and product was collected continuously. The composition of the etherification zone product taken for this study is 2.63 wt % methanol, 10.15 wt % TAME and the remaining unconverted hydrocarbon components of C5-70° C. cut mixed olefinic naphtha. TBA is added precisely in the product and the feed mixture is reacted as per the process conditions mentioned in the table below.

TABLE 4

| Run No. | Pressure (bar) | Temperature (deg C.) | Methanol (wt %) | TBA (wt %) | Ether (wt %) |
|---|---|---|---|---|---|
| 1 | 16 | 50 | 1.7 | 1.2 | 7.8 |
| 2 | 16 | 60 | 1.4 | 1.05 | 7.39 |
| 3 | 16 | 80 | 1.04 | 0.43 | 4.13 |
| 4 | 16 | 100 | 1.08 | 0.64 | 3.12 |
| 5 | 8 | 50 | 1.53 | 2.2 | 10.5 |
| 6 | 8 | 60 | 1.42 | 2.32 | 9.21 |
| 7 | 8 | 70 | 1.28 | 1.76 | 8.78 |
| 8 | 8 | 80 | 1.14 | 1.11 | 5.53 |
| 9 | 6 | 70 | 1.46 | 2.4 | 9.16 |

In the initial attempt, efforts made to keep both the first reaction zone and second reaction zone operating conditions in the similar range in order to minimize the unit operations. However it is observed that at higher pressure of 16 bar and even at low temperature of 50° C., ether yield decreases significantly. Although there is reduction in methanol content from its original value of 2.63 wt % in all the temperature range, it is surprising to note that there is a significant reduction of ether concentration in the product especially at higher temperatures, which is not desirable for the process. This may be attributed due to decomposition of the ether product at higher temperature in presence of TBA. Hence conditions were optimized to reduce the methanol content in the product without compromising the ether concentration in the product. It is found that at 6-8 bar and at temperature in the range of 60-70° C. it is possible to reduce the methanol concentration in the product while maintaining the ether concentration close to first reaction zone product. It is found that both the reaction zones require different atmosphere for promoting the specific desired reactions.

In the present invention both the reaction zones have to be operated at entirely different process conditions to get the desired product with significantly less methanol concentration and with maximum TAME and other ether concentration in the product.

EXAMPLE-6

TABLE 5

GCMS analysis of Mixed ether product samples
COMPOSITE PRDT LP-1089

| S. No. | Component identified | M. F | M. wt | % w/w |
|---|---|---|---|---|
| 1. | Butene | C4H8 | 56 | 1.3 |
| 2. | Butane, 2-methyl- | C5H12 | 72 | 13.9 |
| 3. | 2-Pentene | C5H10 | 70 | 10.3 |
| 4. | 2-Hexene | C6H12 | 84 | 5.8 |
| 5. | Pentane, 2-methyl- | C6H14 | 86 | 9.2 |
| 6. | Pentane, 3-methyl- | C6H14 | 86 | 7.8 |
| 7. | 2-Pentene, 2-methyl- | C6H12 | 84 | 8.5 |
| 8. | 2-Pentene, 3-methyl-, | C6H12 | 84 | 2.0 |
| 9. | 2-Butene, 2,3-dimethyl- | C6H12 | 84 | 3.3 |
| 10. | Methyl-tert-butyl ether | C5H12O | 88 | 2.9 |
| 11. | Benzene | C6H6 | 78 | 0.4 |
| 12. | Tert-amyl methyl ether | C6H14O | 102 | 15.1 |
| 13. | Pentane, 2,2,4-trimethyl- | C8H18 | 114 | 2.6 |
| 14. | Pentene, 2,4,4-trimethyl- | C8H16 | 112 | 2.7 |
| 15. | 1-Hexene, -dimethyl- | C8H16 | 112 | 0.3 |
| 16. | 2-Pentene, -trimethyl- | C8H16 | 112 | 1.4 |
| 17. | Hexane, -dimethyl- | C8H18 | 114 | 0.6 |
| 18. | Hexene, -dimethyl- | C8H16 | 112 | 0.7 |
| 19. | Hexene, -dimethyl- | C8H16 | 112 | 0.3 |
| 20. | Heptane, 4-methyl- | C8H18 | 114 | 0.9 |
| 21. | Heptane, -dimethyl- | C9H20 | 128 | 0.3 |
| 22. | Cyclohexane, 1,3-dimethyl | C8H16 | 112 | 0.6 |
| 23. | C7H16O ether | C7H16O | 116 | 1.8 |
| 24. | C7H16O ether | C7H16O | 116 | 5.2 |
| 25. | Cyclohexane, 1,3-dimethyl-, cis- | C8H16 | 112 | 0.7 |
| 26. | Hexane, 3-methoxy-3-methyl- | C8H18O | 130 | 1.1 |
| 27. | 2-Hexene, 2,3-dimethyl- | C8H16 | 112 | 0.2 |

This example shows the composition of product of present invention analyzed through High resolution Gas chromatography-Mass spectroscopy. This shows the presence of ethers ranging from C5 to C8 which confirms that the higher olefins reacts with methanol and forms the respective ethers in first and second reaction zone. The equilibrium conversion of iso-amylenes is about 70%, as the methanol reacts with iso-amylenes on 1:1 mole ratio, the remaining methanol reacts with other olefins under the specified process conditions and yields various ethers as mentioned in the above table and produces a high octane blending stream with minimum methanol concentration in the product.

EXAMPLE-7

Research Octane Number (RON) of the Product.

Base case stream was analyzed for RON in CFR engine as per ASTM D 2699 and it is found to be 90.8, the product of the present invention has been tested for the RON and it is found to be in the range of 95-97. It is confirmed through repetitive analysis.

Typical feed properties used in the above examples and product properties obtained from the present invention are mention in the table below.

TABLE 6

| | | Product | |
|---|---|---|---|
| | Feed | Product 1 | Product-2 |
| RON by CFR | 90.8 | 96.2 | 96.6 |
| Total Sulfur, ppmw | 20.0 | 26.0 | 25.4 |
| Density, kg/m³ | 653.4 | 671.7 | 679.1 |
| RVP, KPA | 102 | 105 | 102 |
| D86 | | | |
| IBP, ° C. | 31.9 | 29.6 | 30.1 |
| 10% Recovered, ° C. | 36.1 | 37.3 | 37.3 |
| 50% Recovered, ° C. | 39.7 | 47 | 49.3 |
| 90% Recovered, ° C. | 53.6 | 75.6 | 80.6 |
| FBP, ° C. | 65.4 | 102 | 104.8 |

The concentration of iso-amylenes present in the feed may vary from 10-30% which depends upon the type of olefinic refinery streams like coker naphtha, FCC light gasoline, C5 stream from steam cracker etc. and the isoamylene content analyzed for various lots is provided in the below table 7.

TABLE 7

| | Feed (FCCU Light Gasoline) | | | | |
|---|---|---|---|---|---|
| | Lot 1 | Lot 2 | Lot 3 | Lot 4 | Lot 5 |
| Isoamylenes, wt % | 25.542 | 24.32 | 22.71 | 17.9 | 10.5 |

The invention claimed is:

1. A process for production of mixed ethers from mixed olefinic naphtha stream boiling in the range of C5-90° C. cut comprising isoamylene, the process comprising:
   (i) reacting the mixed olefinic naphtha stream with methanol in a first etherification reaction zone, wherein the reaction is carried out at a pressure above 16 bar and the stoichiometric mole ratio of methanol to isoamylene is in the range of 0.5-0.9 to obtain a first product comprising tertiary amyl methyl ether; and
   (ii) reacting the product of step (i) and tertiary butyl alcohol in a second etherification reaction zone to obtain a second product comprising methyl tertiary butyl ether, wherein the first product is cooled prior to reaction in step (ii).

2. The process as claimed in claim 1, wherein the tertiary butyl alcohol is produced in the second etherification reaction zone by reacting mixed olefinic C4 stream with water.

3. The process as claimed in claim 1, wherein the reaction in the first etherification reaction zone is carried out at a pressure in the range of 16-20 bar and at a temperature in the range of 70-90° C.

4. The process as claimed in claim 1, wherein the reaction in the second etherification reaction zone is carried out at a pressure of about 6-8 bar and at a temperature in the range of 60-70° C.

5. The process as claimed in claim 1, wherein the mole ratio of tertiary butyl alcohol to methanol is maintained in the range of 0.5-1 in the second etherification reaction zone.

6. The process as claimed in claim 1, wherein the methanol in the product of first etherification reaction zone is in the range of 0.25-0.5 wt. % and in product of the second etherification reaction zone is in the range of 0.03-0.05 wt. % and tertiary amyl methyl ether in the range of 16 to 18 wt. %.

7. A process for production of mixed ethers from mixed olefinic naphtha stream boiling in the range of C5-90° C. cut comprising isoamylene as claimed in claim 1,
wherein the first product obtained in step (i) is fed into a product separation column to separate heavier ether product from unconverted mixed olefinic naphtha stream and methanol; and
wherein the unconverted product from the product separation column is fed into a second etherification reactor, operating at the same conditions as that of first etherification reaction zone.

* * * * *